(12) United States Patent
Sredni et al.

(10) Patent No.: US 8,080,237 B2
(45) Date of Patent: *Dec. 20, 2011

(54) USE OF TELLURIUM COMPOUNDS FOR PROTECTION FROM ULTRA-VIOLET RADIATION

(76) Inventors: Benjamin Sredni, Kfar-Saba (IL); Michael Albeck, Ramat-Gan (IL)

(*) Notice: Subject to any disclaimer, the term of this patent is extended or adjusted under 35 U.S.C. 154(b) by 557 days.

This patent is subject to a terminal disclaimer.

(21) Appl. No.: 11/992,094

(22) PCT Filed: Sep. 14, 2006

(86) PCT No.: PCT/IL2006/001081
§ 371 (c)(1),
(2), (4) Date: Mar. 14, 2008

(87) PCT Pub. No.: WO2007/032010
PCT Pub. Date: Mar. 22, 2007

(65) Prior Publication Data
US 2009/0269289 A1    Oct. 29, 2009

Related U.S. Application Data

(60) Provisional application No. 60/716,924, filed on Sep. 15, 2005.

(51) Int. Cl.
*A61K 8/00* (2006.01)
*A61K 8/18* (2006.01)
*A61Q 17/04* (2006.01)

(52) U.S. Cl. .......................... 424/59; 424/650; 514/183
(58) Field of Classification Search .................. None
See application file for complete search history.

(56) References Cited

U.S. PATENT DOCUMENTS

| | | | | |
|---|---|---|---|---|
| 4,761,490 | A | * | 8/1988 | Albeck et al. ........... 549/347 |
| 4,764,461 | A | * | 8/1988 | Albeck et al. ........... 435/70.4 |
| 7,045,150 | B2 | | 5/2006 | Strassmann et al. |
| 7,652,065 | B2 | * | 1/2010 | Albeck et al. ........... 514/463 |
| 2010/0055055 | A1 | * | 3/2010 | Albeck et al. ........... 424/59 |

FOREIGN PATENT DOCUMENTS
WO    WO 2007/032009    3/2007

OTHER PUBLICATIONS

Schwarz, T. 2002. Photoimmunosuppression. Photodermatology Photoimmunology & Photomedicine. 18: 141-145.*
Weiss, E., A.J. Mamelak, S. La Morgia, B. Wang, C. Feliciani, A. Tulli, and D.N. Sauder. 2004. The role of interleukin-10 in the pathogenesis and potential treatment of skin diseases. Journal of American Academy of Dermatology. 50: 657-675.*

(Continued)

*Primary Examiner* — Carlos Azpuru
*Assistant Examiner* — David Browe
(74) *Attorney, Agent, or Firm* — Mark M. Friedman

(57) ABSTRACT

Methods for treating skin conditions such as basal cell carcinoma and/or actinic keratosis are provided, which are effected by administering a pharmaceutically effective amount of a tellurium-containing compound. A pharmaceutical composition for treatment of skin conditions such as basal cell carcinoma an/or actinic keratosis is also provided.

9 Claims, 1 Drawing Sheet

OTHER PUBLICATIONS

Kalechman et al. "Role of Endogenous Cytokines Secretion in Radioprotection Conferred by the Immunomodulator Ammonium Trichloro(Dioxyethylene-0-0')Tellurate", Blood, 85(6): 1555-1561, 1995. Abstract, p. 1555, col. 1, Lines 1-4, 6-15, p. 1559, col. 1, Lines 6-9, 12-20, col. 2, Lines 1-10.

International Preliminary Report on Patentability Dated Jan. 2, 2008 From the International Preliminary Examining Authority Re.: Application No. PCT/IL06/01081.

Lima et al. "A Novel Organotellurium Compound (RT-01) as a New Antileishmanial Agent", Korean Journal of Parasitology, 47(3): 213-218, Sep. 2009.

Persike et al. "Protective Effect of the Organotelluroxetane RF-07 in Pilocarpine-Induced Status Epilepticus", Neurobiology of Disease, 31: 120-126, 2008.

* cited by examiner

USE OF TELLURIUM COMPOUNDS FOR PROTECTION FROM ULTRA-VIOLET RADIATION

RELATED APPLICATIONS

This Application is a National Phase of PCT Patent Application No. PCT/IL2006/001081 having International filing date of Sep. 14, 2006, which claims the benefit of U.S. Provisional Patent Application No. 60/716,924 filed on Sep. 15, 2005. The contents of the above Applications are all incorporated herein by reference.

FIELD AND BACKGROUND OF THE INVENTION

The present invention relates to novel therapeutic methods and pharmaceutical compositions for treatment and protection of skin damage caused by ultraviolet (UV) radiation. More particularly, the present invention related to methods utilizing and compositions comprising tellurium containing compounds, which prevent the induction of IL-10 produced by exposure to ultraviolet radiation.

Ultraviolet radiation is electromagnetic radiation of a wavelength shorter than that of the visible light, but longer than that of X-rays. It may be subdivided into UVA (315-380 nanometers), UVB (280-315 nanometers) and UVC (less than 280 nanometers).

The most common consequence of ultraviolet exposure is erythema, or sunburn. Severe sunburn is marked by bright pink or even scarlet-colored skin, swelling, blistering, and extreme pain. An extremely severe case may also be accompanied by nausea, fever or chills, and tachycardia (a racing heart beat). Because of water lost through the skin, sunburns can also lead to dehydration. UV damage apparently triggers an increase of several chemical substances, including prostaglandins and histamines, both of which contribute to inflammation.

Sunburn is primarily caused by UVB rays. UVA rays penetrate deeply and do not cause sunburn, but can contribute to the ageing of the skin, DNA damage and possibly skin cancer. UVA rays are absorbed less efficiently by the atmosphere than UVB. Consequently, the ratio of UVA to UVB will increase as the sun gets lower in the sky.

Long-term exposure to UV rays may also result in sun-damaged skin, even in the absence of sunburn. Much of what was once attributed to aging is now known to be caused by sun damage. Old age can bring about roughness, fine wrinkling, and looseness of the skin. Sun-exposed skin, however, is also marked by coarse wrinkling and elastosis, which gives the skin a pebbly, yellowed quality. Both wrinkling and elastosis are caused by damage to collagen fibers in the lowest level of skin, the dermis.

In addition to these effects, sun-exposed skin is also prone to irregular hyperpigmentation and depigmentation, and actinic keratoses, which are rough, red patches of precancerous skin cells.

As a defense against UV radiation, the body tans when exposed to moderate levels of radiation by releasing melanin, which helps to block UV penetration and prevent damage to the vulnerable lower skin tissues.

Suntan (also referred to herein as sun screen and sun block) preparations that partly blocks UV radiation is widely available. Most sunscreens work by use of an organic material that absorbs UV radiation (such as oxybenzone) or an opaque material that reflects UV rays (such as titanium dioxide, zinc oxide), or a combination thereof. Active ingredients allowable by the FDA in sunblocks include p-aminobenzoic acid, avobenzone, cinoxate, dioxybenzone, homosalate, menthyl anthranilate, octocrylene, octyl methoxycinnamate, octyl salicylate, oxybenzone, padimate, phenylbenzimidazole sulfonic acid, sulisobenzone, titanium oxide, trolamine salicylate and zinc oxide.

Solar radiation in the ultraviolet (UV) range, especially UVA and UVB, may also cause suppression of the skin's immune function (*Frontiers in Bioscience* 2, 1997; 538-551), and may produce a carcinogenic effect. Studies suggest that UVA is important in causing immunosuppression in the skin (*Br J Dermatol*. 2002; 146:933-937). In one indicator of immunosuppression, UV radiation cripples immunity by diminishing the Langerhans cells' number and function (*Proc Natl Acad Sci USA*. 1997, 94:5255-5260; *J Biomed Biotechnol*. 2001; 1:5-6). Langerhans cells exposed to UV in vitro lose the ability to present antigens to T cells (*Proc Natl Acad Sci USA*. 1997; 94:5255-5260). In the skin, Langerhans cells are inhibited by the release of cytokines, such as IL-10. UV irradiation can also convert normal skin chromophores into agents that are immunosuppressive, such as the conversion of transurocanic acid to cis-urocanic acid (*Frontiers in Bioscience* 2, 1997; 538-551).

Immune-response modifiers have been found to induce activation of Toll-like receptors, which leads to production of cytokines and chemokines, such as INF-[alpha], TNF-[alpha], IL-12, MCP-1, and MIP-1[alpha] (*J Exp Med*. 2001; 194:863-870; *J Interferon Cytokine Res*. 1995; 15:537-545). The chemokines attract immune cells to the site of application, and the cytokines cause activation of immune cells. Toll agonists have been found to promote cytokine and chemokine release from dendritic cells that reside in the dermis and the epidermis (*J Exp Med*. 2001; 194:863-870). Activation of immune cells and release of cytokines by these dendritic cells can rally the immune system back into action, overcoming the Langerhans cell deficit (*J Invest Dermatol*. 2000; 114:135-141).

Acute UV damage to keratinocytes usually leads to activation of the tumor-suppressing gene p53, which is responsible for induction of DNA repair and apoptosis (*Frontiers in Bioscience* 2, 1997; 538-551). When the UV exposure is chronic, however, errors associated with DNA repair and/or replication can result in mutations in the p53 gene. The damage caused involves chemical bonding of adjacent pyrimidine bases in the form of dimers. These dimers are of 2 main types: pyrimidine pyrimidone photoproducts between adjacent pyrimidine residues, and cyclobutane dimers between adjacent thymine or cytosine residues. The p53 mutation in keratinocytes plays a key role in the process of carcinogenesis in the skin. In addition to the p53 gene, mutations in another tumor-suppressing gene, the patched (PTCH) gene, seem to be implicated in the formation of skin carcinomas (*Br J Dermatol*. 2002; 146(suppl 61):17-19).

The efficacy of topically applied sunscreens is determined by their ability to inhibit UV-induced erythema. Sunscreens have been assumed to also provide protection against UV-induced carcinogenesis. However, UV exposure causes characteristic immunological alterations in the skin, which might be of direct pathogenic relevance to UV-induced carcinogenesis. Since, according to the present understanding of the immunological and molecular events leading to carcinogenesis of the skin, measurement of UV-induced erythema and vasodilation appears insufficient, so the prevention of UV-induced erythema might, in fact, be biologically irrelevant as an indicator of protection against UV-induced skin cancer.

Various tellurium compounds have been described in the art as having immunomodulating properties. A particularly effective family of tellurium-containing compounds is taught, for example, in U.S. Pat. Nos. 4,752,614; 4,761,490; 4,764,461 and 4,929,739, whereby another effective family, represented by a compound called SAS, is taught, for example, in a recently filed U.S. Provisional Patent Application No. 60/610,660, which are all incorporated by reference as if fully set forth herein. The immunomodulating properties of this family of tellurium-containing compounds is described, for example, in U.S. Pat. Nos. 4,962,207, 5,093, 135, 5,102,908 and 5,213,899, which are all incorporated by reference as if fully set forth herein.

One of the most promising compounds described in these patents is ammonium trichloro(dioxyethylene-O,O') tellurate, which is also referred to herein and in the art as AS101. AS101, as a representative example of the family of tellurium-containing compound discussed hereinabove, exhibits antiviral (*Nat. Immun. Cell Growth Regul.* 7(3):163-8, 1988; *AIDS Res Hum Retroviruses.* 8(5):613-23, 1992), and tumoricidal activity (*Nature* 330(6144):173-6, 1987; *J. Clin. Oncol.* 13(9):2342-53, 1995; *J. Immunol.* 161(7):3536-42, 1998.

It has been suggested that AS101, as well as other tellurium-containing immunomodulators, stimulate the innate and acquired arm of the immune response. For example, it has been shown that AS101 is a potent activator of interferon (IFN) (IFN) in mice (*J. Natl. Cancer Inst.* 88(18):1276-84, 1996) and humans (*Nat. Immun. Cell Growth Regul.* 9(3): 182-90, 1990; *Immunology* 70(4):473-7, 1990; *J. Natl. Cancer Inst.* 88(18):1276-84, 1996.)

It has also been demonstrated that AS101, as well as other tellurium-containing immunomodulators, induce the secretion of a spectrum of cytokines, such as IL-1α, IL-6 and TNF-α, and that macrophages are one main target for AS101 (*Exp. Hematol.* 23(13):1358-66, 1995) and it was found to inhibit IL-10 at the m-RNA level, and this inhibition may cause an increase in IL-12 (*Cell Immunol.* 176(2):180-5, 1997); *J. Natl. Cancer Inst.* 88(18):1276-84, 1996).

Other publications describing the immunomodulation properties of AS101 include, for example, "The immunomodulator AS101 restores T(H1) type of response suppressed by Babesia rodhaini in BALB/c mice". *Cell Immunol* 1998 February; "Predominance of TH1 response in tumor-bearing mice and cancer patients treated with AS101". *J Natl Cancer Inst* 1996 September; "AS-101: a modulator of in vitro T-cell proliferation". *Anticancer Drugs* 1993 June; "The immunomodulator AS101 administered orally as a chemoprotective and radioprotective agent". *Int J Immunopharmacol* 1992 May; "Inhibition of the reverse transcriptase activity and replication of human immunodeficiency virus type 1 by AS 101 in vitro". *AIDS Res Hum Retroviruses* 1992 May; "Immunomodulatory effects of AS101 on interleukin-2 production and T-lymphocyte function of lymphocytes treated with psoralens and ultraviolet A". *Photodermatol Photoimmunol Photomed* 1992 February; "Use and mechanism of action of AS101 in protecting bone marrow colony forming units-granulocyte-macrophage following purging with ASTA-Z". *Cancer Res* 1991 Oct. 15; "The effect of the immunomodulator agent AS101 on interleukin-2 production in systemic lupus erythematosus (SLE) induced in mice by a pathogenic anti-DNA antibody". *Clin Exp Immunol* 1990 March; "Toxicity study in rats of a tellurium based immunomodulating drug, AS-101: a potential drug for AIDS and cancer patients". *Arch Toxicol* 1989; "The biological activity and immunotherapeutic properties of AS-101, a synthetic organotellurium compound". *Nat Immun Cell Growth Regul* 1988; and "A new immunomodulating compound (AS-101) with potential therapeutic application". *Nature* 1987 Nov.

U.S. Pat. No. 4,761,490 discloses a topical formulation of AS101 in petroleum jelly or Oil of Olay, for use as an immunostimulant. U.S. Pat. No. 6,742,381 discloses the use of AS101 in petroleum jelly for treating psoriasis.

In addition to its immunomodulatory effect, AS101 is also characterized by low toxicity. Toxicity tests have shown that LD50 values in rats following intravenous and intramuscular administration of AS101 are 500-1000 folds higher than the immunologically effective dose.

While the immunomodulating effect of tellurium-containing compounds was studied with respect to various aspects thereof, the use of tellurium compounds in the protection of skin against damage caused by ultraviolet radiation has never been suggested nor practiced hitherto.

There is thus a widely recognized need for, and it would be highly advantageous to have, a composition for treatment and protection of the skin against damage caused by ultraviolet radiation having advantages over prior art compositions by inclusion of tellurium containing compounds which prevent the induction of IL-10-induced immunosuppression caused by exposure to ultraviolet radiation.

SUMMARY OF THE INVENTION

The present invention successfully addresses the shortcomings of the presently known methods and compositions for treatment and protection of skin damage caused by ultraviolet radiation by providing methods and compositions comprising tellurium compounds, which are devoid of the side effects of the commonly known methods and treatments for these conditions.

According to one aspect of the present invention there is provided a method of protecting the skin of a subject against damage caused by ultraviolet radiation, the method comprising administering to the subject a therapeutically effective amount of at least one tellurium-containing compound.

According to another aspect of the present invention there is provided a method of prevention or treatment of damage to the skin of a subject caused by ultraviolet radiation, the method comprising administering to the subject a therapeutically effective amount of at least one tellurium-containing compound.

According to yet another aspect of the present invention there is provided a method of prevention of ultraviolet-induced induction of IL-10 in the skin of a subject, the method comprising administering to the subject a therapeutically effective amount of at least one tellurium-containing compound.

According to still another aspect of the present invention there is provided a method of prevention of skin cancer caused by repetitive and/or frequent exposure to ultraviolet-radiation, the method comprising administering to the skin of the subject a therapeutically effective amount of at least one tellurium-containing compound prior to exposure to said ultraviolet-radiation. The cancer may be a carcinoma, such as, for example, basal cell carcinoma, squamous cell carcinoma or melanoma.

According to a further aspect of the present invention there is provided a use of a tellurium-containing compound in the manufacture of a medicament, whereby the medicament can be for protecting the skin of a subject against damage caused by ultraviolet radiation, prevention or treatment of damage to the skin caused by ultraviolet radiation, prevention of ultraviolet-induced induction of IL-10 in the skin and/or prevention of skin cancer caused by repetitive and/or frequent exposure to ultraviolet-radiation.

According to an additional aspect of the present invention there is provided a pharmaceutical composition identified for use in protection of the skin of a subject against damage caused by ultraviolet radiation, comprising at least one tellurium-containing compound and a pharmaceutically acceptable carrier.

According to further features in preferred embodiments of the invention described below, the ultraviolet radiation may optionally have a wavelength in the range of from about 280 to about 315 nanometers (i.e. UVB). Alternatively the ultraviolet radiation may have a wavelength in the range of from about 315 to about 380 nanometers (i.e. UVA). Preferably, the radiation is UVB.

According to still further features in the described preferred embodiments, the damage caused to the skin by the ultraviolet radiation may be, for example, DNA damage, erythema, sun-damage, and suppression of the immune function of the skin.

According to further features in preferred embodiments of the invention described below, the tellurium-containing compound comprises at least one tellurium dioxide moiety and optionally and preferably is at least one of tellurium dioxide ($TeO_2$) per se, an organic complex of $TeO_2$ (as detailed hereinbelow), a compound having general Formula I:

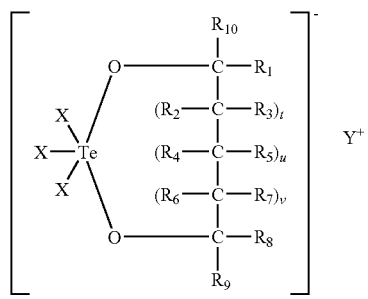

Formula I a compound having general Formula II:

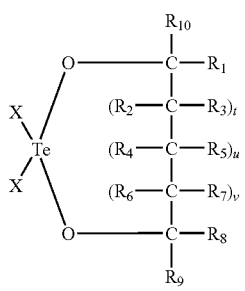

Formula II a compound having general Formula III:

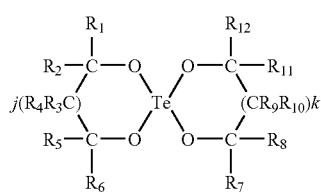

Formula III and
a compound having general Formula IV:

Formula IV wherein:
each of t, u and v is independently 0 or 1;
each of m and n is independently an integer from 0 to 3;
each of j and k is independently an integer from 0 to 4;
Y is selected from the group consisting of ammonium, phosphonium, potassium, sodium and lithium;
X is a halogen atom; and
each of $R_1$-$R_{22}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfonamido.

Preferably, the tellurium-containing compound has general Formula I or general Formula IV.

According to an embodiment in which the tellurium-containing compound has general Formula I, preferably t, u and v are each 0. More preferably, each of $R_1$, $R_8$, $R_9$ and $R_{10}$ is hydrogen; more preferably X is a halogen atom, most preferably the halogen atom is chloro. More preferably, Y is ammonium. The preferred compound according to this embodiment is referred to hereinafter as AS101.

According to an alternative embodiment of this feature of the present invention, the tellurium-containing compound has the general Formula IV. Preferably, according to this embodiment, n and m are each 0. More preferably, each of $R_{15}$, $R_{18}$, $R_{19}$ and $R_{22}$ is hydrogen. The preferred compound according to this embodiment is referred to hereinafter as SAS.

The compounds of the present invention may be administered by any suitable route, such as the oral, rectal, transmucosal, intestinal, parenteral, intrathecal, direct intraventricular, intravenous, intraperitoneal, intranasal, and intraocular routes. Preferably, administration is by the topical route.

In any of the methods or uses described herein, the tellurium-containing compound preferably forms a part of a pharmaceutical composition, as described hereinbelow.

Thus, according to a further aspect of the present invention there is provided a pharmaceutical composition, which comprises the tellurium-containing compound and a pharmaceutically acceptable carrier.

In embodiments wherein the tellurium-containing compound has general Formula I or general Formula IV, the concentration of the tellurium-containing compound preferably ranges from about 0.01 to about 50 weight percentages and preferably between about 0.01 to about 20 weight percentages or even between about 0.01 to about 5 weight percentages of the composition.

For topical administration, the pharmaceutical composition is preferably in the form of a cream, an ointment, a paste, a gel, a lotion, a milk, a suspension, a solution, an aerosol, a spray, a foam, a shampoo, a mousse, a serum, a swab, a pledget, a pad, a tincture, a patch or a soap.

Optionally, the pharmaceutical composition may further comprise at least one additional active agent, including, but not limited to, an antineoplastic agent, an immunomodulator, an interferon and a non-steroidal anti-inflammatory drug (such as oxicams, piroxicam, isoxicam, tenoxicam, sudoxicam, CP-14,304, salicylates, aspirin, disalcid, benorylate, trilisate, safapryn, solprin, diflunisal, fendosal, acetic acid derivatives, diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac, fenamates, mefenamic, meclofenamic, flufenamic, niflumic, tolfenamic acids, propionic acid derivatives, ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, tiaprofen, pyrazoles, phenylbutazone, oxyphenbutazone, feprazone, azapropazone, trimethazone and derivatives, esters, salts and mixtures thereof).

According to still further features in the described preferred embodiments of the methods, uses or compositions of the present invention, the composition may optionally further comprise at least one ingredient selected from the group consisting of a humectant, a deodorant agent, an antiperspirant, a sun screening agent, a sunless tanning agent, a pH adjusting agent, a chelating agent, a preservative, an emulsifier, an occlusive agent, an emollient, a thickener, a solubilizing agent, a penetration enhancer, an anti-irritant, a colorant, a propellant and a surfactant. Most preferably, the additional ingredient comprises at least one of a sun screening agent and a sunless tanning agent.

Non-limiting examples of sun screening agents include p-aminobenzoic acid, salts and derivatives thereof (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl)ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one) and 4-isopropyl-di-benzoylmethane, and any combination thereof.

Non-limiting examples of sunless tanning agents include dihydroxyacetone, glyceraldehyde, indoles and derivatives thereof.

The pharmaceutical composition may be packaged in a packaging material and identified in print, in or on the packaging material, for use in protection of the skin against damage caused by ultraviolet radiation.

According to still further features in the described preferred embodiments, the carrier is selected such that: the tellurium-containing compound, at a concentration of 10 weight percents, is soluble, dispersible and/or suspendable therein; and the formulation is chemically and physically stable upon storage at room temperature for at least 30 days.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

The term "therapeutically effective amount" or "pharmaceutically effective amount" denotes that dose of an active ingredient or a composition comprising the active ingredient that will provide the therapeutic effect for which the active ingredient is indicated.

As used herein a "pharmaceutical composition" refers to a preparation of one or more of the active ingredients described herein, either compounds or physiologically acceptable salts thereof, with other chemical components such as traditional drugs, physiologically suitable carriers and excipients.

As used herein, the term "pharmaceutically acceptable" means approved by a regulatory agency of the Federal or a state government or listed in the U.S. Pharmacopeia or other generally recognized pharmacopeia for use in animals, and more particularly in humans. Herein, the phrases "physiologically suitable carrier" and "pharmaceutically acceptable carrier" are interchangeably used and refer to an approved carrier or a diluent that does not cause significant irritation to an organism and does not abrogate the biological activity and properties of the administered conjugate.

As used herein, the term "carrier" refers to a diluent, adjuvant, excipient, or vehicle with which the therapeutic is administered.

Herein the term "excipient" refers to an inert substance added to a pharmaceutical composition to further facilitate processes and administration of the active ingredients.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
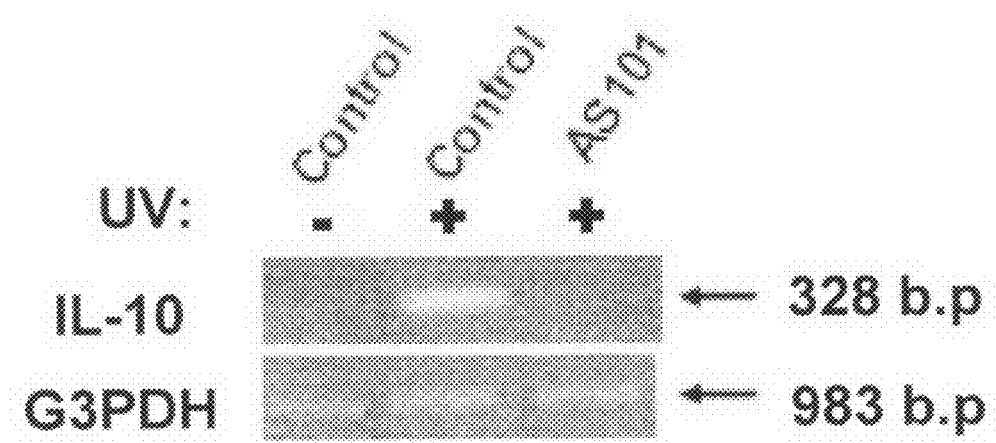
FIG. 1 shows results of reverse transcription-PCR (RT-PCR) analysis for IL-10 and G3PDH, following UV exposure, in the presence and absence of AS101.

The present invention is of novel therapeutic methods and pharmaceutical compositions for treatment and protection of skin damage caused by ultraviolet (UV) radiation. More particularly, the present invention is of methods utilizing and compositions comprising tellurium containing compounds, which prevent the induction of IL-10 caused by exposure to ultraviolet radiation.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The present invention successfully addresses the shortcomings of the presently known methods of treating and protecting the skin against damage caused by ultraviolet radiation by providing methods utilizing and compositions comprising tellurium containing compounds, which prevent the induction of IL-10 caused by exposure to ultraviolet radiation.

Various studies have shown that UVB radiation promotes cutaneous immunosuppression by the release of immunoregulatory cytokines, and by depletion of Langerhans cells. It has further been suggested that such cytokines, especially IL-10, play an important role in the development of skin cancer.

While conceiving the present invention, it was thus envisioned that since UV radiation increases IL-10 production in the skin, and since tellurium containing compounds such as AS101 and SAS may inhibit the production of IL-10, and are further characterized as substantially non-toxic agents, these tellurium-containing compounds, as well as other tellurium compounds of this family, could serve as potent agents for the treatment and protection of the skin against damage caused by ultraviolet radiation by preventing the induction of IL-10-induced immunosuppression caused by exposure to ultraviolet radiation.

As demonstrated in the Examples section below, it was indeed found that tellurim-containing compounds such as AS101 can prevent the induction of IL-10-production.

The present invention therefore provides a method of protecting the skin of a subject against damage caused by ultraviolet radiation, comprising administering a therapeutically effective amount of at least one tellurium-containing compound.

The ultraviolet radiation may be in the range of from about 280 to about 315 nanometers (i.e. UVB), or in the range of from about 315 to about 380 nanometers (i.e. UVA). Preferably, the radiation is UVB.

The damage caused to the skin by the ultraviolet radiation may be, for example, DNA damage, erythema, sun-damage, and suppression of the immune function of the skin.

The present invention further provides a method of prevention or treatment of damage to the skin of a subject caused by ultraviolet radiation, comprising administering a therapeutically effective amount of at least one tellurium-containing compound.

The present invention further provides a method of prevention of ultraviolet-induced induction of IL-10 in the skin of a subject, comprising administering a therapeutically effective amount of at least one tellurium-containing compound.

The present invention further provides a method of prevention of skin cancer caused by repetitive and/or frequent exposure to ultraviolet-radiation, comprising administering a therapeutically effective amount of at least one tellurium-containing compound prior to exposure to said ultraviolet-radiation. The cancer may be a carcinoma, such as, for example, basal cell carcinoma, squamous cell carcinoma or melanoma The present invention further provides a pharmaceutical composition identified for use in protection of the skin of a subject against damage caused by ultraviolet radiation, comprising at least one tellurium-containing compound and a pharmaceutically acceptable carrier.

As used herein, the phrase "tellurium-containing compound" encompasses any compound that includes one or more tellurium atoms and exhibits immunomodulating properties.

The phrase "immunomodulating properties" includes any effect of the compound on the immune response of a subject. Exemplary immunomodulating properties can be manifested, for example, by an effect on cytokines secretion, interleukins production, lymphocytes function, and the like.

Preferably, the tellurium-containing compound includes at least one tellurium dioxide moiety.

Thus, the compound can be, for example, an inorganic tellurium-containing compound such as, for example, tellurium dioxide ($TeO_2$) per se.

The compound can alternatively be an organic tellurium-containing compound which includes one or more tellurium atoms and one or more organic moieties that are attached thereto.

Representative examples of inorganic tellurium-containing compounds that were shown to exert immunomodulating properties and hence are particularly useful in the context of the present invention include, for example, $TeO_2$ per se. Also included are compounds that form $TeO_2$ in aqueous solutions, preferably in the form of an organic complex such as, for example, a $TeO_2$ complex with citric acid or ethylene glycol. A representative example of the latter is the complex $TeO_2 \cdot HOCH_2CH_2OH \cdot NH_4Cl$.

Organic tellurium-containing compounds that were shown to exert immunomodulating properties and hence are particularly useful in the context of the present invention include, for example, ammonium salts, or any other salts, of halogenated tellurium-containing compounds having a bidentate cyclic moiety attached to the tellurium atom. The bidentate cyclic moiety is preferably a di-oxo moiety having two oxygen atoms attached to the tellurium atom. Alternatively, the bidentate cyclic moiety can be a di-thio moiety, in which two sulfur atoms are attached to the tellurium atom.

Preferred compounds in this category are collectively represented by the general Formula I:

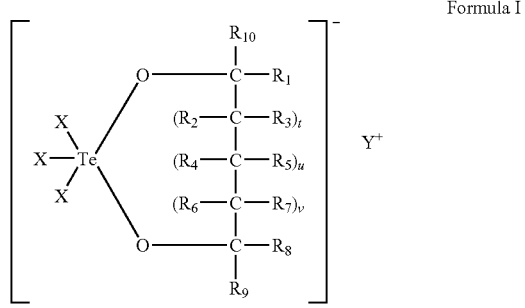

Formula I

In the general Formula I above, each of t, u and v is independently 0 or 1, such that the compound may include a five-membered ring, a six-membered ring, or a seven-membered ring. Preferably, each of t, u and v is 0, such that the compound includes a five-membered ring.

X is a halogen atom, as described hereinabove, and is preferably chloro.

Y is selected from the group consisting of ammonium, phosphonium, potassium, sodium and lithium, and is preferably ammonium.

Each of $R_1$-$R_{10}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, alkoxy, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfoneamido.

As used herein, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 5 carbon atoms. The alkyl group may be substituted or unsubstituted. When substituted, the substituent group can be, for example, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, sulfonamide, phosphonyl, phosphinyl, carbonyl, thiocarbonyl, carboxy, thiocarboxy, carbamate, thiocarbamate, amido, sulfonamido, and amino, as these terms are defined herein.

As used herein, the term "hydroxyalkyl" refers to an alkyl, as this term is defined herein, substituted by a hydroxy group, as defined herein, and includes, for example, hydroxymethyl, hydroxyethyl, hydroxypropyl and hydroxy-n-butyl.

As used herein, the term "halogen", which is also referred to herein interchangeably as "a halogen atom" or "halo", includes chloro (Cl), bromo (Br), iodo (I) and fluoro (F).

The term "haloalkyl" refers to an alkyl, as this term is defined herein, substituted by a halogen, as defined herein, and includes, for example, chloromethyl, 2-iodoethyl, 4-bromo-n-butyl, iodoethyl, 4-bromo-n-pentyl and the like.

The term "alkanoyloxy" refers to a carbonyl group, as define herein and includes, for example, acetyl, propionyl, butanoyl and the like.

The term "carboxyalkyl" refers to an alkyl, as this term is defined herein, substituted by a carboxy group, as defined herein, and includes, for example, carboxymethyl, carboxyethyl, ethylenecarboxy and the like.

The term "alkylcarbonylalkyl" refers to an alkyl, as this term is defined herein, substituted by a carbonyl group, as defined herein, and includes, for example, methanoylmethyl, ethanoylethyl and the like.

The term "amidoalkyl" refers to an alkyl, as this term is defined herein, substituted by an amide group, as defined herein, and includes, for example, —$CH_2CONH_2$; —$CH_2CH_2CONH_2$; —$CH_2CH_2CH_2CONH_2$ and the like.

The term "cyanoalkyl" refers to an alkyl, as this term is defined herein, substituted by an cyano group, as defined herein, and includes, for example, —$CH_2CN$; —$CH_2CH_2CN$; —$CH_2CH_2CH_2CN$ and the like.

The term "N-monoalkylamidoalkyl" refers to an alkyl, as this term is defined herein, substituted by an amide group, as defined herein, in which one of R' and R" is an alkyl, and includes, for example, —$CH_2CH_2CONHCH_3$, and —$CH_2CONHCH_2CH_3$.

The term N,N-dialkylamidoalkyl refers to an alkyl, as this term is defined herein, substituted by an amide group, as defined herein, in which both R' and R" are alkyl, and includes, for example, —CH$_2$CON(CH$_3$)$_2$; CH$_2$CH$_2$CON (CH$_2$—CH$_3$)$_2$ and the like.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, phosphonyl, phosphinyl, carbonyl, thiocarbonyl, carboxy, thiocarboxy, carbamate, thiocarbamate, amido, sulfonamido, and amino, as these terms are defined herein.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, phosphonyl, phosphinyl, phosphonium, carbonyl, thiocarbonyl, carboxy, thiocarboxy, carbamate, thiocarbamate, amido, sulfonamido, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, phosphonyl, phosphinyl, phosphonium, carbonyl, thiocarbonyl, carboxy, thiocarboxy, carbamate, thiocarbamate, amido, sulfonamido, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, phosphonyl, phosphinyl, phosphonium, carbonyl, thiocarbonyl, carboxy, thiocarboxy, carbamate, thiocarbamate, amido, sulfonamido, and amino, as these terms are defined herein. Representative examples are piperidine, piperazine, tetrahydro furane, tetrahydropyrane, morpholino and the like.

A "hydroxy" group refers to an —OH group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" group refers to a —C(=O)—R' group, where R' is hydrogen, alkyl, alkenyl, cycloalkyl, aryl, heteroaryl (bonded through a ring carbon) or heteroalicyclic (bonded through a ring carbon) as defined herein.

A "thiocarbonyl" group refers to a —C(=S)—R' group, where R' is as defined herein for R'.

A "carboxy" group refers to a —C(=O)—O—R' or a —O—C(=O)—R' group, where R' is as defined herein.

A "sulfinyl" group refers to an —S(=O)—R' group, where R' is as defined herein.

A "sulfonyl" group refers to an —S(=O)$_2$—R' group, where R' is as defined herein.

A "sulfate" group refers to a —O—S(=O)$_2$—OR' group, where R' is as defined herein.

A "sulfonamido" group refers to a —S(=O)$_2$—NR'R" group or a R'S(=O)$_2$—NR", with R' is as defined herein and R" is as defined for R'.

A "carbamyl" or "carbamate" group refers to an —OC(=O)—NR'R" group or a R"OC(=O)—NR'— group, where R' and R" are as defined herein.

A "thiocarbamyl" or "thiocarbamate" group refers to an —OC(=S)—NR'R" group or an R"OC(=S)NR'— group, where R' and R" are as defined herein.

An "amino" group refers to an —NR'R" group where R' and R" are as defined herein.

An "amido" group refers to a —C(=O)—NR'R" group or a R'C(=O)—NR" group, where R' and R" are as defined herein.

A "nitro" group refers to an —NO$_2$ group.

A "cyano" group refers to a —C≡N group.

The term "phosphonyl" describes a —O—P(=O)(OR')(OR") group, with R' and R" as defined hereinabove.

The term "phosphinyl" describes a —PR'R" group, with R' and R" as defined hereinabove.

As cited hereinabove, the compounds in this category are salts of organic tellurium-containing compounds. The salts can be, for example, ammonium salts, phsophonium salts and alkaline salts such as potassium salts, sodium salts, lithium salts and the like.

Hence, Y in Formula I above can be a phosphonium group, as defined herein, an ammonium group, as defined herein, potassium (K$^+$), sodium (Na$^+$) or lithium (Li$^+$).

As used herein, the term "phosphonium" describes a —P+R'R"R'" group, with R' and R" as defined herein and R'" is as defined for R'. The term "phsophonium", as used herein, further refers to a —P$^+$R$_6$ group, wherein each of the six R substituents is independently as defined herein for R, R" and R'".

The term "ammonium" describes a —N$^+$R'R"R'" group, with R', R" and R'" as defined herein.

More preferred compounds in this category include compounds having the general Formula I described above, in which Y is ammonium or phosphonium, t, u and v are each 0, and each of $R_1$, $R_8$, $R_9$ and $R_{10}$ is independently hydrogen or alkyl. These compounds can be represented by the following structure:

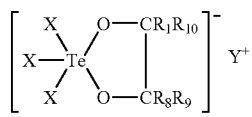

wherein each of $R_1$, $R_8$, $R_9$ and $R_{10}$ is independently hydrogen or alkyl, whereas a preferred alkyl is methyl, and X is halogen, preferably chloro.

The presently most preferred compound for use in the context of the present invention has the following structure:

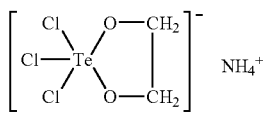

This compound is ammonium trichloro(dioxyethylene-O,O')tellurate, which is also referred to herein and in the art as AS101.

Additional representative examples of organic tellurium-containing compound that are suitable for use in the context of the present invention include halogenated tellurium having a bidentate cyclic moiety attached to the tellurium atom. The bidentate cyclic moiety is preferably a di-oxo ligand having two oxygen atoms attached to the tellurium atom. Alternatively, the bidentate cyclic moiety can be a di-thio ligand, in which two sulfur atoms are attached to the tellurium atom.

Preferred compounds in this category can be represented by the general Formula II:

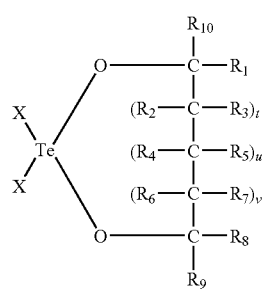

wherein t, u, v, X and $R_1$-$R_{10}$ are as defined hereinabove.

More preferred compounds are those in which t, u, and v are each 0, and X is chloro, such as, but not limited to, the compound having the following structure:

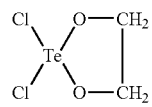

The above compound is also known and referred to herein as AS103.

The organic tellurium-containing compounds having Formulae I and II can be readily prepared by reacting tetrahalotelluride such as $TeCl_4$ with a dihydroxy compound, as is described in detail in U.S. Pat. Nos. 4,752,614, 4,761,490, 4,764,461 and 4,929,739, which are incorporated by reference as if fully set forth herein.

Additional representative examples of organic tellurium-containing compounds that are suitable for use in the context of the present invention include compounds in which two bidentate cyclic moieties are attached to the tellurium atom. Preferably, each of the cyclic moieties is a di-oxo moiety. Alternatively, one or more of the cyclic moieties is a di-thio moiety.

Preferred compounds in this category are collectively represented by the general Formula III:

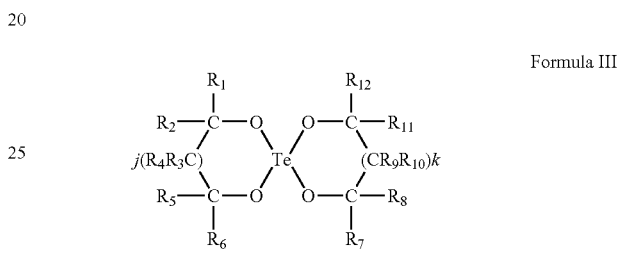

Formula III

In the general Formula III above, each of j and k is independently an integer from 0 to 4, such that the compound may include a five-membered ring, a six-membered ring, a seven-membered ring, an eight-membered ring and/or a nine-membered ring. Preferably, each of j and k is an integer from 0 to 2, such that the compound includes a five-membered ring, a six-membered ring and/or a seven-membered ring. More preferably, each of j and k is 0.

$R_1$-$R_{12}$ are as defined hereinabove for $R_1$-$R_{10}$.

More preferred compounds in this category are those in which j and k are each 0, and $R_3$, $R_4$, $R_9$ and $R_{10}$ are each hydrogen, having the following structure:

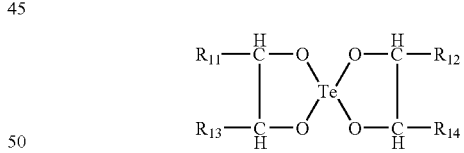

wherein each of $R_{11}$-$R_{14}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, alkoxy, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfoneamido, as these terms are defined herein.

The most preferred compound in this category is a compound in which each of $R_{11}$-$R_{14}$ is hydrogen. This compound is also known as AS102.

Additional representative examples of organic tellurium-containing compounds that are suitable for use in the context of the present invention include the recently disclosed bis-tellurium compounds having general Formula IV:

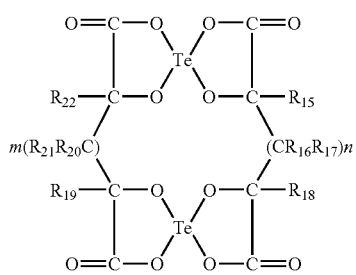

Formula IV wherein each of $R_{15}$-$R_{22}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, alkoxy, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfoneamido, as these terms are defined herein; and m and n are each an integer from 0 to 3.

Preferred compounds in this category are those in which m and n are each 0.

The presently most preferred compound in this family is a compound in which $R_{15}$, $R_{18}$, $R_{19}$ and $R_{22}$ are all hydrogen, referred to hereinafter as SAS, and which has the following structure:

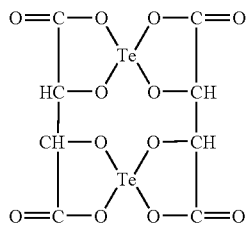

Compounds having the general Formula IV can be readily prepared by reacting substantially equimolar amounts of a tellurium tetralkoxide and a polycarboxylic acid. These materials are combined in the presence of a water free organic solvent such as dried ethanol, dimethyl sulfoxide, i-propanol and the like. Generally the reaction may take place at ambient conditions but if desired higher or lower temperatures and higher or lower pressures may be utilized.

Exemplary tellurium tetraalkoxide compounds that are usable in the preparation of the compounds having general Formula IV above include, without limitation, tetramethoxide, tetraethoxide, tetrapropoxide, tetraisopropoxide, tetrabutoxide, and tetrapentoxide tellerium compounds.

Useful polycarboxylic acids include also polyhydroxy polycarboxylic and hydroxy polycarboxylic acids. Exemplary polycarboxylic acids that are usable in the preparation of the compounds having general Formula IV above include, without limitation, tartaric acid, glutaric acid, succinic acid, malonic acid, gluconic acid and the like.

Additional organic tellurium-containing compounds that are suitable for use in the context of the present invention include those having the general Formula V:

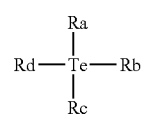

Formula V wherein each of Ra, Rb, Rc and Rd is independently selected from the group consisting of halogen alkyl, aryl, cycloalkyl, alkoxy, aryloxy, thioalkoxy, thioaryloxy, carboxy, carbonyl, thiocarboxy, thiocarbonyl, carbamyl, and thiocarbamyl, as these terms are defined hereinabove, whereby at least one of Ra—Rd is not halogen, namely, is selected from the group consisting of alkyl, aryl, cycloalkyl, alkoxy, aryloxy, thioalkoxy, thioaryloxy, carboxy, carbonyl, thiocarboxy, thiocarbonyl, carbamyl, and thiocarbamyl.

Compounds in this category include those in which one of Ra, Rb, Rc and Rd is halogen alkyl, aryl, cycloalkyl, alkoxy, aryloxy, thioalkoxy, thioaryloxy, carboxy, carbonyl, thiocarboxy, thiocarbonyl, carbamyl, or thiocarbamyl, whereby the others are halogen atoms, e.g., chloro.

Other compounds in this category include those in which two or three of Ra, Rb, Rc and Rd are as described above and the others are halogens e.g., chloro.

Other compounds in this category include those in which each of Ra, Rb, Rc and Rd is as described hereinabove.

According to a further aspect of the present invention there is provided a pharmaceutical composition, which comprises the tellurium-containing compound and a pharmaceutically acceptable carrier.

The compounds described above can be administered or otherwise utilized in this and other aspects of the present invention, either as is or as a pharmaceutically acceptable salt thereof.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound.

The compounds described above can be administered to a subject for treatment and protection of the skin against damage caused by ultraviolet radiation by any of various systemic routes.

Suitable routes of systemic administration may, for example, include the inhalation, oral, buccal, rectal, transmucosal, transdermal, intradermal, transnasal, intestinal and/or parenteral routes; the intramuscular, subcutaneous and/or intramedullary injection routes; the intrathecal, direct intraventricular, intravenous, intraperitoneal, intranasal, and/or intraocular injection routes; and/or the route of direct injection into a tissue region of a subject of the present invention.

Optionally and preferably, the compounds described above can be administered to a subject for treatment and protection of the skin against damage caused by ultraviolet radiation by local routes, and more preferably, the compounds are administered topically.

The term "protection" refers to prevention or reduction of the risk of developing damage caused by ultraviolet radiation, such as skin cancer and/or other skin proliferative pathologies, such as basal cell carcinoma, actinic keratosis, sunburn and skin ageing.

Topical application of the tellurium-containing compounds described herein is preferably effected by applying a pharmaceutically effective amount of a tellurium-containing compound onto a selected skin area.

The selected area can be, for example, an area of the face, ears, neck, scalp, shoulder, back, forearm, hand, chest or leg.

Herein, the phrase "selected area" encompasses the area to be treated and/or protected as well as the tissues surrounding the indicated area. The topical application is effected on and around the selected area.

The term "therapeutically effective amount" or "pharmaceutically effective amount" denotes that dose of an active ingredient or a composition comprising the active ingredient that will provide the therapeutic effect for which the active ingredient is indicated. Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

When administering systemically, a therapeutically effective amount of the tellurium-containing compounds described herein may range, for example, from about 0.01 mg/m$^2$/day to about 20.0 mg/m$^2$/day and thus can be for example, 0.01 mg/m$^2$/day, 0.02 mg/m$^2$/day, 0.03 mg/m$^2$/day, 0.04 mg/m$^2$/day, 0.05 mg/m$^2$/day, 0.1 mg/m$^2$/day, 1 mg/m$^2$/day, 10 mg/m$^2$/day, and 20 mg/m$^2$/day. Preferably, for systemic administration, a therapeutically effective amount of a compound of formula I, II or III ranges from about 0.01 mg/m$^2$/day to about 10.0 mg/m$^2$/day. Also preferably, a therapeutically effective amount of a compound of formula IV for systemic administration ranges from about 0.017 mg/m$^2$/day to about 17 mg/m$^2$/day.

Preferably, when administered parenterally, the therapeutically effective amount is 0.01 mg/m$^2$/day and higher and thus can be, for example, 0.05 mg/m$^2$/day, 0.1 mg/m$^2$/day, 0.2 mg/m$^2$/day, 0.5 mg/m$^2$/day, 0.6 mg/m$^2$/day, 0.7 mg/m$^2$/day, 0.8 mg/m$^2$/day, 0.9 mg/m$^2$/day, 1.0 mg/m$^2$/day, 2.0 mg/m$^2$/day, 3.0 mg/m$^2$/day, 4.0 mg/m$^2$/day, 5.0 mg/m$^2$/day, and up to 20.0 mg/m$^2$/day.

When administered orally to a human subject, a daily dose typically ranges between 0.1 mg and 200 mg, depending on weight and age of the subject. The total daily dose may be administered as a single dosage, or may be divided into a number of separate doses, such as, for example 0.75 mg twice daily, 1 mg three times daily.

As used herein, the term "about" refers to ±10%.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The method according to this aspect of the present invention can further comprise, in addition to administering the tellurium-containing compounds described above, co-administration of an additional active agent. The co-administration can be effected prior to, concomitant with or subsequent to the administration of the tellurium-containing compound. The additional active agent is used for providing an additive beneficial effect in terms of the ailment being treated, conditions associated with the ailment being treated or other parameters such as psychological effects and prophylactic effects.

Hence, exemplary additional active agents according to this embodiment of present invention include, without limitation, one or more, or any combination of an antibiotic agent, an antimicrobial agent, an anti-acne agent, an anti-aging agent, a wrinkle-reducing agent, a skin whitening agent, a sebum reducing agent, an antibacterial agent, an antifungal agent, an antiviral agent, a steroidal anti-inflammatory agent, a non-steroidal anti-inflammatory agent, an anesthetic agent, an antipruriginous agent, an antiprotozoal agent, an antioxidant, an antineoplastic agent, an immunomodulator, an interferon, an antidepressant, an anti histamine, a vitamin, a hormone and an anti-dandruff agent.

Examples of these include alpha-hydroxy acids and esters, beta-hydroxy acids and ester, polyhydroxy acids and esters, kojic acid and esters, ferulic acid and ferulate derivatives, vanillic acid and esters, dioic acids (such as sebacid and azoleic acids) and esters, retinol, retinal, retinyl esters, hydroquinone, t-butyl hydroquinone, mulberry extract, licorice extract, and resorcinol derivatives.

Suitable anti-acne agents for use in this context of the present invention include, without limitation, keratolytics such as salicylic acid, sulfur, glycolic, pyruvic acid, resorcinol, and N-acetylcysteine and retinoids such as retinoic acid and its derivatives (e.g., cis and trans, esters).

Suitable antibiotics for use in this context of the present invention include, without limitation, benzoyl peroxide, octopirox, erythromycin, zinc, tetracyclin, triclosan, azelaic acid and its derivatives, phenoxy ethanol and phenoxy proponol, ethylacetate, clindamycin and meclocycline; sebostats such as flavinoids; alpha and beta hydroxy acids; and bile salts such as scymnol sulfate and its derivatives, deoxycholate and cholate.

Representative examples of non-steroidal anti-inflammatory agents that are usable in this context of the present invention include, without limitation, oxicams, such as piroxicam, isoxicam, tenoxicam, sudoxicam, and CP-14,304; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the dermatologically acceptable salts and esters of these agents. For example, etofenamate, a flufenamic acid derivative, is particularly useful for topical application.

Representative examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Suitable antipruritic agents include, without limitation, pharmaceutically acceptable salts of methdilazine and trimeprazine.

Non-limiting examples of anesthetic drugs that are suitable for use in context of the present invention include pharmaceutically acceptable salts of lidocaine, bupivacaine, chlorprocaine, dibucaine, etidocaine, mepivacaine, tetracaine, dyclonine, hexylcaine, procaine, cocaine, ketamine, pramoxine and phenol.

Suitable antimicrobial agents, including antibacterial, antifungal, antiprotozoal and antiviral agents, for use in context of the present invention include, without limitation, beta-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, streptomycin, tobramycin, and miconazole. Also included are tetracycline hydrochloride, farnesol, erythromycin estolate, erythromycin stearate (salt), amikacin sulfate, doxycycline hydrochloride, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, parachlorometa xylenol, nystatin, tolnaftate and clotrimazole and mixtures thereof.

Non-limiting examples of anti-oxidants that are usable in the context of the present invention include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the trade name Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

Non-limiting examples of antineoplastic agents usable in context of the present invention include daunorubicin, doxorubicin, idarubicin, amrubicin, pirarubicin, epirubicin, mitoxantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A and XR9576.

Non-limiting examples of antidepressants usable in context of the present invention include norepinephrine-reuptake inhibitors ("NRIs"), selective-serotonin-reuptake inhibitors (SSRIs), monoamine-oxidase inhibitors (MAOIs), serotonin-and-noradrenaline-reuptake inhibitors ("SNFIs"), corticotropin-releasing factor (CRF) antagonists, α-adrenoreceptor antagonists, NK1-receptor antagonists, $5-HT_{1A}$-receptor agonist, antagonists, and partial agonists and atypical antidepressants, as well as norepinephrine-reuptake inhibitors such as, but are not limited to amitriptyline, desmethylamitriptyline, clomipramine, doxepin, imipramine, imipramine-oxide, trimipramine; adinazolam, amiltriptylinoxide, amoxapine, desipramine, maprotiline, nortriptyline, protriptyline, amineptine, butriptyline, demexiptiline, dibenzepin, dimetacrine, dothiepin, fluacizine, iprindole, lofepramine, melitracen, metapramine, norclolipramine, noxiptilin, opipramol, perlapine, pizotyline, propizepine, quinupramine, reboxetine, tianeptine, and serotonin-reuptake inhibitors such as, but are not limited to, binedaline, m-chloropiperzine, citalopram, duloxetine, etoperidone, femoxetine, fluoxetine, fluvoxamine, indalpine, indeloxazine, milnacipran, nefazodone, oxaflazone, paroxetine, prolintane, ritanserin, sertraline, tandospirone, venlafaxine and zimeldine.

Exemplary anti-dandruff ingredients usable in context of the present invention include, without limitation, zinc pyrithione, shale oil and derivatives thereof such as sulfonated shale oil, selenium sulfide, sulfur; salicylic acid, coal tar, povidone-iodine, imidazoles such as ketoconazole, dichlorophenyl imidazolodioxalan, clotrimazole, itraconazole, miconazole, climbazole, tioconazole, sulconazole, butoconazole, fluconazole, miconazolenitrite and any possible stereo isomers and derivatives thereof such as anthralin, piroctone olamine (Octopirox), selenium sulfide, and ciclopirox olamine, and mixtures thereof.

Non-limiting examples of vitamins usable in context of the present invention include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin $B_3$ (niacinamide and its derivatives), alpha hydroxy acids (such as glycolic acid, lactic acid, tartaric acid, malic acid, citric acid, etc.) and beta hydroxy acids (such as salicylic acid and the like).

Non-limiting examples of dermatological active ingredients usable in context of the present invention include jojoba oil and aromatic oils such as methyl salicylate, wintergreen, peppermint oil, bay oil, eucalyptus oil and citrus oils, as well as ammonium phenolsulfonate, bismuth subgallate, zinc phenolsulfonate and zinc salicylate. Non-limiting examples of antifungal agents include miconazole, clotrimazole, butoconazole, fenticonasole, tioconazole, terconazole, sulconazole, fluconazole, haloprogin, ketonazole, ketoconazole, oxinazole, econazole, itraconazole, terbinafine, nystatin and griseofulvin.

Non-limiting examples of antihistamines usable in context of the present invention include chlorpheniramine, brompheniramine, dexchlorpheniramine, tripolidine, clemastine, diphenhydramine, promethazine, piperazines, piperidines, astemizole, loratadine and terfenadine.

Suitable hormones for use in the context of the present invention include, for example, androgenic compounds and progestin compounds.

Representative examples of androgenic compounds include, without limitation, methyltestosterone, androsterone, androsterone acetate, androsterone propionate, androsterone benzoate, androsteronediol, androsteronediol-3-acetate, androsteronediol-17-acetate, androsteronediol 3-17-diacetate, androsteronediol-17-benzoate, androsteronedione, androstenedione, androstenediol, dehydroepiandrosterone, sodium dehydroepiandrosterone sulfate, dromostanolone, dromostanolone propionate, ethylestrenol, fluoxymesterone, nandrolone phenpropionate, nandrolone decanoate, nandrolone furylpropionate, nandrolone cyclohexane-propionate, nandrolone benzoate, nandrolone cyclohexanecarboxylate, androsteronediol-3-acetate-1-7-benzoate, oxandrolone, oxymetholone, stanozolol, testosterone, testosterone decanoate, 4-dihydrotestosterone, 5α-dihydrotestosterone, testolactone, 17α-methyl-19-nortestosterone and pharmaceutically acceptable esters and salts thereof, and combinations of any of the foregoing.

Representative examples of progestin compounds include, without limitation, desogestrel, dydrogesterone, ethynodiol diacetate, medroxyprogesterone, levonorgestrel, medroxyprogesterone acetate, hydroxyprogesterone caproate, norethindrone, norethindrone acetate, norethynodrel, allylestrenol, 19-nortestosterone, lynoestrenol, quingestanol acetate, medrogestone, norgestrienone, dimethisterone, ethisterone, cyproterone acetate, chlormadinone acetate, megestrol acetate, norgestimate, norgestrel, desogrestrel, trimegestone, gestodene, nomegestrol acetate, progesterone, 5α-pregnan-3β,20α-diol sulfate, 5α-pregnan-3β,20β-diol sulfate, 5α-pregnan-3β-ol-20-one, 16,5α-pregnen-3β-ol-20-one, 4-pregnen-20β-ol-3-one-20-sulfate, acetoxypregnenolone, anagestone acetate, cyproterone, dihydrogesterone, fluorogestone acetate, gestadene, hydroxyprogesterone acetate, hydroxymethylprogesterone, hydroxymethyl progesterone acetate, 3-ketodesogestrel, megestrol, melengestrol acetate, norethisterone and mixtures thereof.

In any of the different embodiments of the method of the present invention, the tellurium-containing compounds described herein can be provided to a subject either per se, or as part of a pharmaceutical composition where it is mixed with a pharmaceutically acceptable carrier.

Hence, according to another aspect of the present invention there is provided a pharmaceutical composition, which comprises a tellurium-containing compound as described herein and a pharmaceutically acceptable carrier.

Preferably, a concentration of tellurium-containing compound of formula I, II or III in the carrier ranges from about 0.01 weight percent to about 50 weight percents, more preferably from about 0.1 weight percents to about 25 weight percents, of the total weight of the composition. Also preferably, a concentration of tellurium-containing compound of formula IV in the carrier ranges from about 0.017 weight percent to about 85 weight percents, more preferably from about 0.1 weight percents to about 42 weight percents of the total weight of the composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to the subject treated.

Hereinafter, the phrases "physiologically acceptable carrier" and "pharmaceutically acceptable carrier" which may be interchangeably used refer to a carrier or a diluent that does not cause significant irritation to the subject and does not abrogate the biological activity and properties of the administered compound. As used herein, the term "carrier" refers to a diluent, adjuvant, excipient, or vehicle with which the therapeutic is administered.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethyl-cellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise glass, or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Hence, in a preferred embodiment of the present invention, the pharmaceutical composition is formulated in a form suitable for topical application on the treated area.

By selecting the appropriate carrier and optionally other ingredients that can be included in the composition, as is detailed hereinbelow, the compositions of the present invention may be formulated into any form typically employed for topical application. Hence, the compositions of the present invention can be, for example, in a form of a cream, an ointment, a paste, a gel, a lotion, a milk, a suspension, an aerosol, a spray, a foam, a serum, a swab, a pledget, a pad, a patch and a soap.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emolliency). As with other carriers or vehicles, an ointment base should be inert, stable, nonirritating and nonsensitizing. As explained in *Remington: The Science and Practice of Pharmacy*, 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semiliquid preparations in which solid particles, including the active agent, are present in a water or alcohol base. Lotions are typically preferred for treating large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethyl-cellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to *Remington: The Science and Practice of Pharmacy*, supra, for further information.

Pastes are semisolid dosage forms in which the bioactive agent is suspended in a suitable base. Depending on the nature of the base, pastes are divided between fatty pastes or those made from a single-phase aqueous gels. The base in a fatty paste is generally petrolatum, hydrophilic petrolatum and the like. The pastes made from single-phase aqueous gels generally incorporate carboxymethylcellulose or the like as a base. Additional reference may be made to *Remington: The Science and Practice of Pharmacy*, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol.; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or hydroalcoholic, but are typically formulated with high alcohol content which, upon application to the skin of a user, quickly evaporates, driving the active ingredient through the upper skin layers to the site of treatment.

Skin patches typically comprise a backing, to which a reservoir containing the active agent is attached. The reservoir can be, for example, a pad in which the active agent or composition is dispersed or soaked, or a liquid reservoir. patches typically further include a frontal water permeable adhesive, which adheres and secures the device to the treated region. Silicone rubbers with self-adhesiveness can alternatively be used. In both cases, a protective permeable layer can be used to protect the adhesive side of the patch prior to its use. Skin patches may further comprise a removable cover, which serves for protecting it upon storage.

Examples of pharmaceutically acceptable carriers that are suitable for pharmaceutical compositions for topical applications include carrier materials that are well-known for use in the cosmetic and medical arts as bases for e.g., emulsions, creams, aqueous solutions, oils, ointments, pastes, gels, lotions, milks, foams, suspensions, aerosols and the like, depending on the final form of the composition.

Representative examples of suitable carriers according to the present invention therefore include, without limitation, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions.

Other suitable carriers according to the present invention include, without limitation, alcohols, such as, for example, monohydric and polyhydric alcohols, e.g., ethanol, isopropanol, glycerol, sorbitol, 2-methoxyethanol, diethyleneglycol, ethylene glycol, hexyleneglycol, mannitol, and propyleneglycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

When the pharmaceutical composition according to the present invention is formulated for topical application, the concentration of the tellurium-containing compound of formula I, II or III preferably ranges from about 0.01 weight percent and about 50 weight percents, more preferably from about 0.1 to about 25 weight percents, and the concentration of the tellurium-containing compound of formula IV preferably ranges from about 0.015 to about 85 weight percents, of the total weight of the composition.

Thus, depending on the condition being treated and the composition form, the concentration of the tellurium-containing compound can be, for example, 0.01 weight percent, 0.05 weight percent, 0.1 weight percent, 0.5 weight percent, 1 weight percent, 2 weight percents, 3 weight percents, 4 weight percents or 5 weight percents. Higher concentrations can also be used and thus the concentration of the tellurium-containing compound can be, for example, 5 weight percents, 6 weight percents, 7 weight percents, 8 weight percents, 9 weight percents or 10 weight percents, and can further be, for example, 20 weight percents, 25 weight percents, 30 weight percents, 40 weight percents, 50 weight percents, 60 weight percents, 70 weight percents, 80 weight percents, and up to 85 weight percents of the total weight of the composition.

A formulation of a tellurium-containing compound, which is particularly useful for topical application of the active compound, and more particularly, for obtaining stable compositions that comprise relatively high concentration of a tellurium-containing compound, has been recently designed by the present assignee. This formulation is described in detail in a U.S. Provisional Patent Application No. 60/843, 402 filed Sep. 11, 2006, and entitled "Topical Formulations of tellurium-containing compounds", to the present assignee, which is incorporated by reference as if fully set forth herein. This formulation is based on a carrier selected such that: the tellurium-containing compound, at a concentration of 10 weight percents, is soluble, dispersible and/or suspendable therein; and the formulation is chemically and physically stable upon storage at room temperature for at least 30 days.

Hence, in preferred embodiments of the present invention, any of the pharmaceutical compositions described herein comprises a carrier as described in the above-mentioned U.S. Provisional Patent Application No. 60/843,402 filed Sep. 11, 2006.

Each of the pharmaceutical compositions described herein may further comprise, according to an embodiment of the present invention an additional active agent, as described hereinabove.

Each of the pharmaceutical compositions described herein can optionally further comprise a variety of components that are suitable for providing the compositions with additional usage benefits. Such conventional optional components are well known to those skilled in the art and are referred to herein as "ingredients". Some non-limiting representative examples of these ingredients include humectants, deodorants, antiperspirants, sun screening agents, sunless tanning agents, hair conditioning agents, pH adjusting agents, chelating agents, preservatives, emulsifiers, occlusive agents, emollients, thickeners, solubilizing agents, penetration enhancers, anti-irritants, colorants, propellants and surfactants.

Preferably, the ingredient comprises at least one of a sun screening agent and a sunless tanning agent.

Thus, for example, the compositions of the present invention can comprise humectants or moisturizing agents. Representative examples of humectants that are usable in this context of the present invention include, without limitation, guanidine, glycolic acid and glycolate salts (e.g. ammonium slat and quaternary alkyl ammonium salt), aloe vera in any of its variety of forms (e.g., aloe vera gel), allantoin, urazole, polyhydroxy alcohols such as sorbitol, glycerol, hexanetriol, propyleneglycol, butylene glycol, hexylene glycol and the like, polyethylene glycols, sugars and starches, sugar and starch derivatives (e.g., alkoxylated glucose), hyaluronic acid, lactamide monoethanolamine, acetamide monoethanolamine and any combination thereof.

The compositions of the present invention can further comprise a pH adjusting agent. The addition of a pH adjusting agent is particularly preferred when the compositions are applied topically on the skin. The pH of these treated areas is typically lower than 6.0. Hence, it is preferable for the compositions of the present invention to have a pH value of between about 4 and about 7, preferably between about 4 and about 6, so as to avoid irritations to the skin or induction of imbalance of the bacteria population if the genital areas. Suitable pH adjusting agents include, for example, one or more of adipic acids, glycines, citric acids, calcium hydroxides, magnesium aluminometasilicates, buffers or any combinations thereof.

Representative examples of deodorant agents that are usable in the context of the present invention include, without limitation, quaternary ammonium compounds such as cetyltrimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmIthyl sarcosine, lauroyl sarcosine, N-myristoyl glycine, potassium N-lauryl sarcosine, stearyl, trimethyl ammonium chloride, sodium aluminum chlorohydroxy lactate, tricetylmethyl ammonium chloride, 2,4,4'-trichloro-2'-hydroxy diphenyl ether, diaminoalkyl amides such as L-lysine hexadecyl amide, heavy metal salts of citrate, salicylate, and piroctose, especially zinc salts, and acids thereof, heavy metal salts of pyrithione, especially zinc pyrithione and zinc phenolsulfate. Other deodorant agents include, without limitation, odor absorbing materials such as carbonate and bicarbonate salts, e.g. as the alkali metal carbonates and bicarbonates, ammonium and tetraalkylammonium carbonates and bicarbonates, especially the sodium and potassium salts, or any combination of the above.

Antiperspirant agents can be incorporated in the compositions of the present invention either in a solubilized or a particulate form and include, for example, aluminum or zirconium astringent salts or complexes.

Representative examples of sun screening agents usable in context of the present invention include, without limitation, p-aminobenzoic acid, salts and derivatives thereof (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl)ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one) and 4-isopropyl-di-benzoyl-methane, and any combination thereof.

Representative examples of sunless tanning agents usable in context of the present invention include, without limitation, dihydroxyacetone, glyceraldehyde, indoles and their derivatives. The sunless tanning agents can be used in combination with the sunscreen agents.

The chelating agents are optionally added to the compositions of the present invention so as to enhance the preservative or preservative system. Preferred chelating agents are mild agents, such as, for example, ethylenediaminetetraacetic acid (EDTA), EDTA derivatives, or any combination thereof.

Suitable preservatives that can be used in the context of the present composition include, without limitation, one or more alkanols, disodium EDTA (ethylenediamine tetraacetate), EDTA salts, EDTA fatty acid conjugates, isothiazolinone, parabens such as methylparaben and propylparaben, propyleneglycols, sorbates, urea derivatives such as diazolindinyl urea, or any combinations thereof.

Suitable emulsifiers that can be used in the context of the present invention include, for example, one or more sorbitans, alkoxylated fatty alcohols, alkylpolyglycosides, soaps, alkyl sulfates, monoalkyl and dialkyl phosphates, alkyl sulphonates, acyl isothionates, or any combinations thereof.

Suitable occlusive agents that can be used in the context of the present invention include, for example, petrolatum, mineral oil, beeswax, silicone oil, lanolin and oil-soluble lanolin derivatives, saturated and unsaturated fatty alcohols such as behenyl alcohol, hydrocarbons such as squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Suitable emollients, that can be used in the context of the present invention include, for example, dodecane, squalane, cholesterol, isohexadecane, isononyl isononanoate, PPG Ethers, petrolatum, lanolin, safflower oil, castor oil, coconut oil, cottonseed oil, palm kernel oil, palm oil, peanut oil, soybean oil, polyol carboxylic acid esters, derivatives thereof and mixtures thereof.

Suitable thickeners that can be used in the context of the present invention include, for example, non-ionic water-soluble polymers such as hydroxyethylcellulose (commercially available under the Trademark Natrosol® 250 or 350), cationic water-soluble polymers such as Polyquat 37 (commercially available under the Trademark Synthalen® CN), fatty alcohols, fatty acids and their alkali salts and mixtures thereof.

Representative examples of solubilizing agents that are usable in this context of the present invention include, without limitation, complex-forming solubilizers such as citric acid, ethylenediamine-tetraacetate, sodium meta-phosphate, succinic acid, urea, cyclodextrin, polyvinylpyrrolidone, diethylammonium-ortho-benzoate, and micelle-forming solubilizers such as TWEENS and spans, e.g., TWEEN 80. Other solubilizers that are usable for the compositions of the present invention are, for example, polyoxyethylene sorbitan fatty acid ester, polyoxyethylene n-alkyl ethers, n-alkyl amine n-oxides, poloxamers, organic solvents, phospholipids and cyclodextrines.

Suitable penetration enhancers usable in context of the present invention include, but are not limited to, dimethylsulfoxide (DMSO), dimethyl formamide (DMF), allantoin, urazole, N,N-dimethylacetamide (DMA), decylmethylsulfoxide ($C_{10}$ MSO), polyethylene glycol monolaurate (PEGML), propyleneglycol (PG), propyleneglycol monolaurate (PGML), glycerol monolaurate (GML), lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. The permeation enhancer may also be a vegetable oil. Such oils include, for example, safflower oil, cottonseed oil and corn oil.

Suitable anti-irritants that can be used in the context of the present invention include, for example, steroidal and non steroidal anti-inflammatory agents or other materials such as aloe vera, chamomile, alpha-bisabolol, cola nitida extract, green tea extract, tea tree oil, licoric extract, allantoin, caffeine or other xanthines, glycyrrhizic acid and its derivatives.

The compositions of the present invention may be packed or presented in any convenient way. For example, they may be packed in a tube, a bottle, or a pressurized container, using techniques well known to those skilled in the art and as set forth in reference works such as Remington's Pharmaceutical Science $15^{th}$ Ed. It is preferred that the packaging is done in such a way so as to minimize contact of the unused compositions with the environment, in order to minimize contamination of the compositions before and after the container is opened.

The compositions are preferably identified in print, in or on the packaging material, for use in the prevention or treatment of skin damage caused by ultraviolet radiation, as described hereinabove.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Induction of Suction Blisters

In normal volunteers, suction blisters were induced by vacuum and heat on normal skin, or on UVB-irradiated skin of volar forearms 24 h after exposure. Single cell suspensions of epidermal cells were prepared by limited trypsinization of the blister roof. Briefly, epidermal sheets were washed in PBS (Biofluids. Roekville. MD) and floated in 0.5% trypsin (United Stares Biochemical Corp. Cleveland. OH) for 45 min al 37° C., transferred to HBSS (Biofluids) containing 0.05 DNase (Sigma Chemical Co. SI. Louis. MO) and 10% heat-inactivated pooled human $AB^+$ serum (Sigma Chemical Co.) and disaggregated by repeated aspirations and expulsions through a syringe. Cells were then passed through a 100 μm nylon mesh and washed 3 times in PBS (Biofluids). Dry cell pellet were stored at −70° C. until mRNA extraction.

Example 2

UVB Irradiation In Vivo

UVB irradiation in vivo was performed with 4 FS20 fluorescent lamps (Sylvania. Springfield. Va.) that emit wavelengths between 280 and 320 nm with a peak at 313 nm. Light intensity was determined using an IL-770 Germicidal-Erythemal radiometer (international Light Inc. Newburyport. Me.) equipped with a sensor and a 313-nm filter. In vivo irradiation was performed on volar forearms of normal volunteers after prior determination of their minimal erythema dose. Two areas (approximately 3.0 cm² each) on the right forearm were irradiated with UVB that one area was treated with AS101 (4% in Vaseline) and the other one with Vaseline alone. After 24 h. blisters were induced at the two irradiated sites and blister roofs of approximately 0.8 cm² each were removed. Blisters were also induced on the non-irradiated (control) left forearm.

Example 3

Extraction of mRNA

The frozen pellets of epidermal cells were dissolved by repeated pipetting 800 μl of lysis bufer and transferred to RNase-free Eppendorf tubes containing 500 μg of superparamagnetic polystyrene Dynaheads Oligo(dT)$_{25}$ (Dynal. Great Neck. N.Y.). The beads had been previously washed twice with lysis bufer using a Dynal MPC magnet (Dynal). Preparations containing both beads and epidermal cell extracts were then incubated on ice for 5 min and washed twice in washing. Two final washings were performed in washing bufer without SDS. poly (A+). RNA was then released from the beads by heating for 2 min al 65° C. in distilled RNase-free water and the beads were removed using the Dynal MPC magnet. The concentration of mRNA was measured on a Beckman DU-64 spectrophotometer employing a 5 μl Ultra microcell.

Example 4

Reverse Transcription-PCR (RT-PCR) for IL-10 and G3PDH

Thirty ng mRNA for IL-10 transcription and 3 ng mRNA for glyceraldehyde-3-phosphate-dehydrogenase (G3PDH) transcription was reverse transcribed by specific priming to first strand cDNA using the GeneAmp RNA-PCR kit (Perkin-Elmer Cetus. Norwalk. CT). Briefly, 3 μl mRNA suspended in distilled RNase-free water was added to 15 μl of RT-mixture. consisting of 1 μl 20 mM of the anti-sense oligonucleotide. The mixture was then heated to (65° C. for 3 min and chilled on ice. Fifty, units Moloney murine leukemia virus reverse transcriptase and 20 units RNase inhibitor was added, and the mixture was heated at 42° C. for 30 min. Reverse transcription was stopped by heating at 99° C. for 5 min. To control for genomic DNA contamination. the reaction was regularly performed in the absence of reverse transcriptase.

Amplification of cDNA was performed by PCR as described before. Eighty μl of a PCR master mix, and 1 μl 20 mM of the sense oligonucleotide were added to the first strand cDNA product contained in the 20 μl RT-mixture. Amplification was conducted in thin-walled GeneAmp reaction tubes (Perkin-Elmer Cetus) using the "hot start" technique with AmpliWax PCR Gems (Perkin-Elmer Cetus) to prevent mispriming and primer dimerization. Thermal cycling was performed with a Perkin-Elmer Cetus DNA Thermal Cyeler 9600 programmed for 35 cycles (IL10) and 20 cycles (G3PDH), respectively; each cycle consisted of 94° C. for 15 s and 720 for 75 s. which were the optimal amplification conditions as determined in prior titration studies. Oligonucleotide primers and positive cDNA template controls for human IL-IO and G3PDH were obtained from Clontech Laboratories (Palo Alto. CA). and were constructed to span two or more introns. The predicted size of the amplified cDNA products were 328 bp for IL-10 and 983 bp for G3PDH.

Example 5

Induction of IL-10 Gene Expression by In Vivo UVB Exposure of Epidermal Cells To demonstrate the effect of UVB on IL-10 gene expression in epidermal cells, four volunteers were UVB irradiated on their right forearms. The left forearms of two subjects were treated with 3% AS101 in petroleum jelly U.S.P. and the left forearms of the other two treated with petroleum jelly U.S.P. alone. Twenty-four hours after UVB exposure, suction blisters were induced, epidermal cell suspensions were prepared, mRNA was extracted and RT-PCR for IL-10 and G3PDH transcripts was performed as described above. It was determined that epidermal cells from the volunteers that were not treated with UVB did not express IL-10. The epidermal cells of the UVB treated patients show a strong IL-10 transcription. Volunteer treated with AS101 before UVB show a significant decrease of IL-10 compare to the UVB (FIG. 1).

These results demonstrate that tellurium-containing compounds can prevent the induction of IL-10. Since UVB is know to increase IL-10 production in the skin, the results obtained point to the effectiveness of tellurium-containing compounds in providing protection against damage to the skin that could be caused by Il-10 production induced by UV radiation.

Example 6

Sunscreen Cream Composition Comprising AS101

An exemplary composition according to the present embodiments is as follows:

| % by weight | |
|---|---|
| 5 | AS101 |
| 10 | Octyl methoxycinnamate |
| 6 | PEG-7-hydrogenated castor oil |
| 6 | Titanium dioxide |
| 5 | Isoamyl p-methoxycinnamate |
| 5 | Propyleneglycol |
| 3 | Jojoba oil |
| 3 | 4-Methylbenzylidenecamphor |
| 2 | PEG-45/dodecyl glycol copolymer |
| 1 | Dimethicone |
| 0.5 | PEG-40-hydrogenated castor oil |
| 0.5 | Tocopheryl acetate |
| 0.5 | Phenoxyethanol |
| 0.2 | EDTA |
| 52.3 | Water |

Example 7

Sunscreen Gel Composition Comprising AS101

An exemplary composition according to the present embodiments is as follows:

| % by weight | |
|---|---|
| 5 | AS101 |
| 8 | Octyl methoxycinnamate |
| 7 | Titanium dioxide |
| 5 | Glycerol |
| 5 | PEG-25 PABA |
| 1 | 4-Methylbenzylidenecamphor |
| 0.4 | Acrylate C10-C30 alkyl acrylate crosspolymer |
| 0.30 | Imidazolidinylurea |
| 0.25 | Hydroxyethylcellulose |
| 0.25 | Sodium methylparaben |
| 0.20 | Disodium EDTA |
| 0.15 | Fragrance |
| 0.15 | Sodium propylparaben |
| 0.10 | Sodium hydroxide |
| 67.2 | Water |

Example 8

Sunscreen Milk Composition Comprising AS101

An exemplary composition according to the present embodiments is as follows:

| % by weight | |
|---|---|
| 5 | AS101 |
| 10 | Mineral oil |
| 6 | PEG-7-hydrogenated castor oil |
| 5 | Isopropyl palmitate |
| 3.5 | Octyl methoxycinnamate |
| 3 | Caprylic/capric triglyceride |
| 3 | Jojoba oil |
| 2 | PEG-45/dodecyl glycol copolymer |
| 0.7 | Magnesium sulfate |
| 0.6 | Magnesium stearate |
| 0.5 | Tocopheryl acetate |
| 0.3 | Glycerol |
| 0.2 | Methylparaben |
| 0.15 | Propylparaben |
| 0.05 | Tocopherol |
| 61 | Water |

Example 9

Sunscreen Composition Comprising SAS

An exemplary composition according to the present embodiments is as follows:

| % by weight | |
|---|---|
| 8.5 | SAS |
| 15 | C12/C15 Alkyl benzoate |
| 0.5 | Butylmethoxydibenzoylmethane |
| 5 | Oxyethylenated acrylic acid/monostearyl itaconate copolymer |
| 0.5 | Triethanolamine |
| 1.5 | Preservatives |
| 69 | Water |

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of protecting the skin of a subject against damage by reducing a risk of damage caused by ultraviolet radiation, wherein said ultraviolet radiation has a wavelength in the range of from about 280 to about 380 nanometers, the method comprising administering to the subject a therapeutically effective amount of at least one tellurium-containing compound, wherein said at least one tellurium-containing compound is a compound having general Formula III:

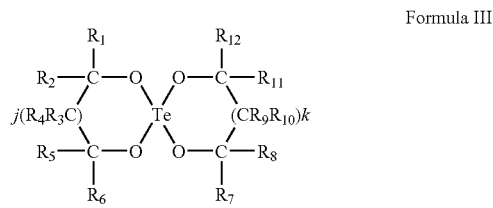

Formula III wherein:
each of j and k is independently an integer from 1 to 4; and
each of $R_1$, $R_2$, $R_3$, $R_4$, $R_5$, $R_6$, $R_7$, $R_8$, $R_9$, $R_{10}$, $R_{11}$ and $R_{12}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfoneamido except each of $R_3$, $R_4$, $R_9$, and $R_{10}$ is not hydrogen.

2. The method of claim 1, wherein said damage is selected from the group consisting of DNA damage, erythema, sun-damage, and suppression of the immune function of the skin.

3. The method of claim 2, wherein:
each of $R_1$, $R_8$, $R_9$ and $R_{10}$ is hydrogen.

4. A method of protecting the skin of a subject against damage caused by ultraviolet radiation, wherein said ultraviolet radiation has a wavelength in the range of from about 280 to about 380 nanometers and wherein said damage is selected from the group consisting of DNA damage, erythema, sun-damage, and suppression of the immune function of the skin, the method comprising administering to the subject a therapeutically effective amount of at least one tellurium-containing compound wherein said tellurium-containing compound is a compound having general Formula IV:

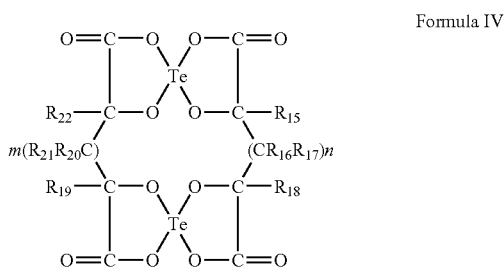

Formula IV wherein:
each of m and n is independently an integer from 0 to 3; and
each of $R_{15}$-$R_{22}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfonyl, sulfate, amine, aryl, heteroaryl, phosphate, phosphonate and sulfoneamido.

5. The method of claim 4, wherein:
n and m are each 0; and
each of $R_{15}$, $R_{18}$, $R_{19}$ and $R_{22}$ is hydrogen.

6. A method of treatment of damage to the skin of a subject caused by ultraviolet radiation, wherein said ultraviolet radiation has a wavelength in the range of from about 280 to about 380 nanometers, the method comprising administering to the subject a therapeutically effective amount of at least one tellurium-containing compound, wherein said at least one tellurium-containing compound is a compound having general Formula III:

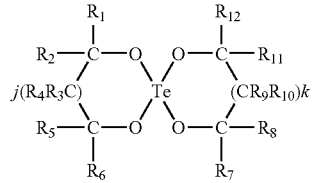

Formula III wherein:
each of j and k is independently an integer from 1 to 4; and
each of $R_1$, $R_2$, $R_3$, $R_4$, $R_5$, $R_6$, $R_7$, $R_8$, $R_9$, $R_{10}$, $R_{11}$ and $R_{12}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfoneamido except each of $R_3$, $R_4$, $R_9$, and $R_{10}$ is not hydrogen.

7. The method of claim 6, wherein said damage is selected from the group consisting of DNA damage, erythema, sundamage, and suppression of the immune function of the skin.

8. A method of treatment of damage to the skin of a subject caused by ultraviolet radiation, wherein said ultraviolet radiation has a wavelength in the range of from about 280 to about 380 nanometers, the method comprising administering to the subject a therapeutically effective amount of at least one tellurium-containing compound wherein said tellurium-containing compound is a compound having said general Formula IV:

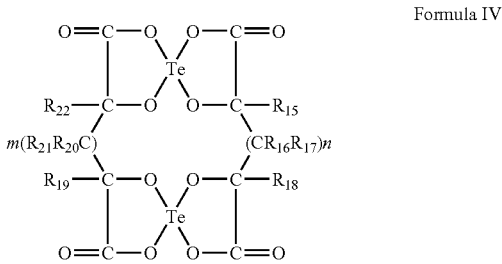

Formula IV wherein:
each of m and n is independently an integer from 0 to 3; and
each of $R_{15}$-$R_{22}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfonyl, sulfate, amine, aryl, heteroaryl, phosphate, phosphonate and sulfoneamido.

9. The method of claim 8, wherein:
n and m are each 0; and
each of $R_{15}$, $R_{18}$, $R_{19}$ and $R_{22}$ is hydrogen.

* * * * *

UNITED STATES PATENT AND TRADEMARK OFFICE
CERTIFICATE OF CORRECTION

| | | |
|---|---|---|
| PATENT NO. | : 8,080,237 B2 | Page 1 of 1 |
| APPLICATION NO. | : 11/992094 | |
| DATED | : December 20, 2011 | |
| INVENTOR(S) | : Benjamin Sredni et al. | |

It is certified that error appears in the above-identified patent and that said Letters Patent is hereby corrected as shown below:

Column 36

Claim 4 line 63 should be corrected as follows:
Change
-- each of in and n.... --
to
"each of m and n...."

Signed and Sealed this
Twenty-eighth Day of February, 2012

David J. Kappos
*Director of the United States Patent and Trademark Office*